United States Patent
Hwang et al.

(10) Patent No.: US 12,274,704 B2
(45) Date of Patent: Apr. 15, 2025

(54) 9,11-SECOSTEROIDS AND THE USE OF 9,11-SECOSTEROIDS IN PREPARING PHARMACEUTICAL COMPOSITIONS FOR INHIBITING INFLAMMATION

(71) Applicant: Chang Gung University of Science and Technology, Taoyuan (TW)

(72) Inventors: Tsong-Long Hwang, Taoyuan (TW); Yu-Chia Chang, Taoyuan (TW); Kuei-Hung Lai, Taoyuan (TW)

(73) Assignee: Chang Gung University of Science and Technology, Taoyuan (TW)

( * ) Notice: Subject to any disclaimer, the term of this patent is extended or adjusted under 35 U.S.C. 154(b) by 65 days.

(21) Appl. No.: 17/242,317

(22) Filed: Apr. 28, 2021

(65) Prior Publication Data

US 2022/0040199 A1 Feb. 10, 2022

(30) Foreign Application Priority Data

Aug. 7, 2020 (TW) .................. 109126808

(51) Int. Cl.
*A61K 31/56* (2006.01)
*A61P 29/00* (2006.01)

(52) U.S. Cl.
CPC .............. *A61K 31/56* (2013.01); *A61P 29/00* (2018.01)

(58) Field of Classification Search
CPC ................................ A61K 31/56; A61P 29/00
See application file for complete search history.

(56) References Cited

U.S. PATENT DOCUMENTS 6,046,041 A * 4/2000 Kerr .................. C12P 19/56
435/189

OTHER PUBLICATIONS

Chang et al (Mar. Drugs, 2020; 18:271 pp. 1-10, published May 21, 2020) (Year: 2020).*
Minh et al (Bioorganic & Medicinal Chemistry Letters, 2011; 21:2155-2159) (Year: 2011).*
Gong et al (Molecular Cancer, 2013; 12:154 pp. 1-14) (Year: 2013).*

* cited by examiner

*Primary Examiner* — Rayna Rodriguez
(74) *Attorney, Agent, or Firm* — Hannah Tien

(57) ABSTRACT

A method for inhibiting inflammatory in a subject is provided, comprising: administering a pharmaceutical composition comprising an effective amount of 9,11-secosteroids.

6 Claims, 5 Drawing Sheets

⌒⌒: NOESY correlation

9,11-SECOSTEROIDS AND THE USE OF 9,11-SECOSTEROIDS IN PREPARING PHARMACEUTICAL COMPOSITIONS FOR INHIBITING INFLAMMATION

CROSS REFERENCE

This application claims the benefit of TW patent Application No. 109126808, filed Aug. 7, 2020, which application is incorporated herein by reference.

FIELD OF THE INVENTION

The present invention is related to a method for inhibiting inflammation by compounds extracted from coral. Particularly, the present invention is related to a method for inhibiting inflammation by 9,11-secosteroids.

BACKGROUND OF THE INVENTION

Inflammation is one aspect of the regular host reaction to injury or infection caused by toxic chemicals, dead cells, pathogens, irritants, or allergens. Neutrophils play an important role in a variety of infectious and inflammatory diseases so as to become an attractive target for therapeutic interventions.

A lot of herbs and plant-derived compounds have been found to alleviate inflammation; however, very few sources have been identified in marine environments. Soft corals are reported to produce a variety of secondary metabolites with diverse pharmacological activities. Most of the metabolites from soft corals are sesquiterpenes, diterpenes, and steroids.

The soft coral *Sinularia leptoclados* belongs to the order Alcyonacea, which has been shown to produce a remarkable diversity of steroids in large quantities. The 9,11-secosteroids found in marine invertebrates such as sponges, corals, ascidians, and mollusks can be structurally characterized by the C-9/11 oxidative cleavage of the C-ring. The potent inhibitory effects of 9,11-secosteroids toward neutrophilic inflammation motivated the current study of chemical compositions with this structural feature.

SUMMARY OF THE INVENTION

The present invention provides a method for inhibiting inflammation in a subject by administering a pharmaceutical composition comprising an effective amount of 9,11-secosteroids; wherein the 9,11-secosteroids having a chemical formula (I):

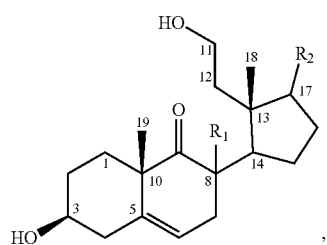
(I)

while R1 is α-H, R2 is

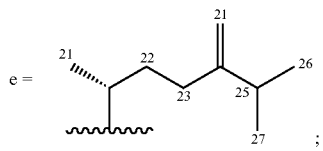

and
while R1 is β-H, R2 is selected from

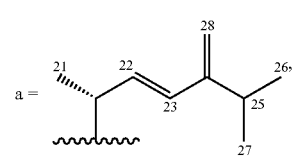

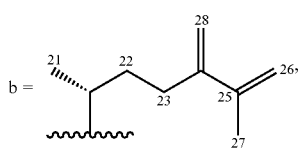

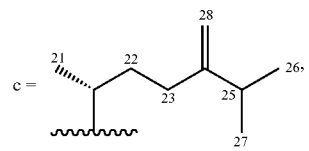

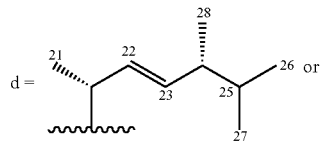

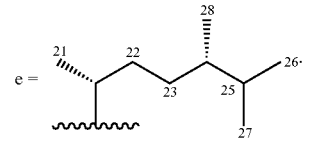

DETAILED DESCRIPTION OF THE INVENTION

Figure 1:
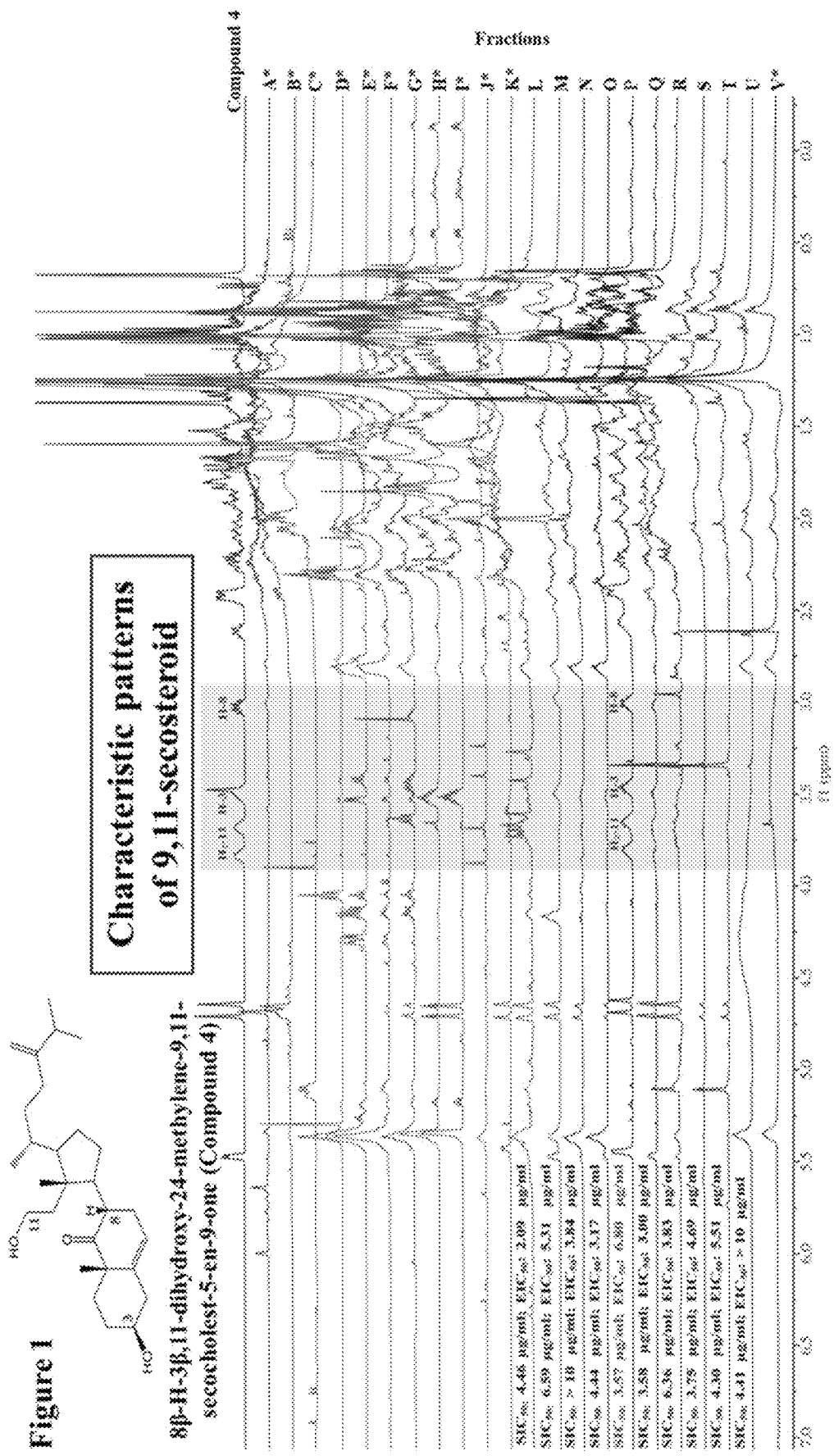
FIG. 1 illustrates $^1$H-NMR spectra of fractions derived from the EtOAc extract of *Sinularia leptoclados* as well as their corresponding inhibitory effects on superoxide anion generation ($SIC_{50}$) and elastase release ($EIC_{50}$) in N-formylmethionyl-leucyl-phenylalanine (fMLF)/cytochalasin B (CB)-induced human neutrophils. The label "*" indicates that both $SIC_{50}$ and $EIC_{50}$ are over 10 μg/mL.

The present invention provides a 9,11-secosteroids having a chemical formula (I):

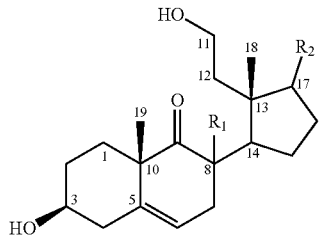

(I)

wherein R1 is β-H, R2 is selected from

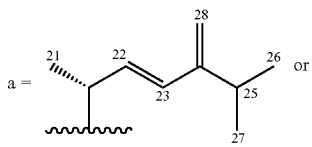

or

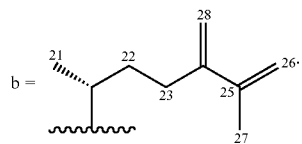

The present invention also provides a pharmaceutical composition, comprising an effective amount of 9,11-secosteroids having a chemical formula (I):

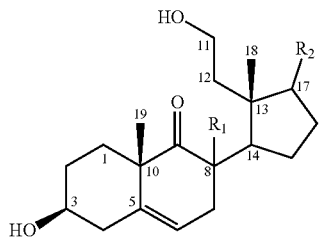

(I)

and a pharmaceutically acceptable carrier or excipient, wherein R1 is β-H, R2 is selected from

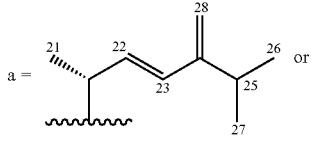

or

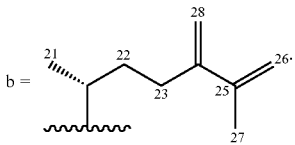

The present invention also provides a method for inhibiting inflammation in a subject, comprising: administering a pharmaceutical composition comprising an effective amount of 9,11-secosteroids, wherein the 9,11-secosteroids having a chemical formula (I):

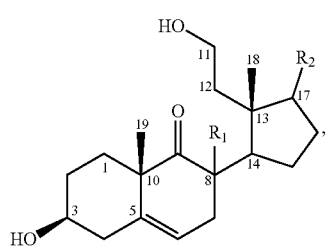

(I)

while R1 is α-H, R2 is

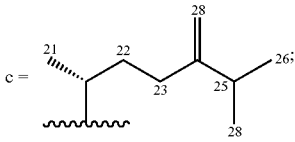

and while R1 is β-H, R2 is selected from

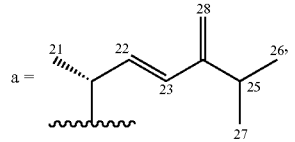

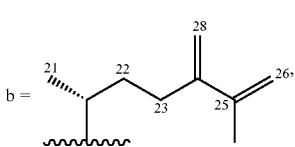

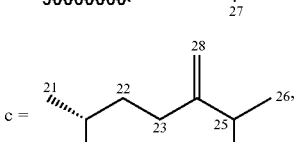

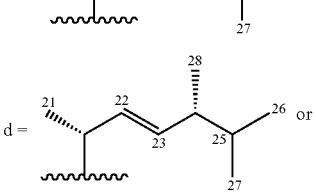

or

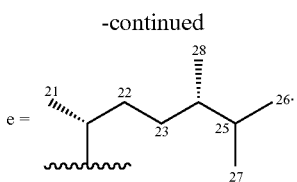

In a preferred embodiment, the pharmaceutical composition for inhibiting inflammation in the present invention is a pharmaceutical compositions for inhibiting superoxide anion generation in human neutrophils.

In a preferred embodiment, the pharmaceutical composition for inhibiting inflammation in the present invention is a pharmaceutical compositions for inhibiting elastase release in human neutrophils.

In a more preferred embodiment, the 9,11-secosteroids in the present invention is 8α-H-3β,11-dihydroxy-24-methylene-9,11-secocholest-5-en-9-one with a chemical formula (IV):

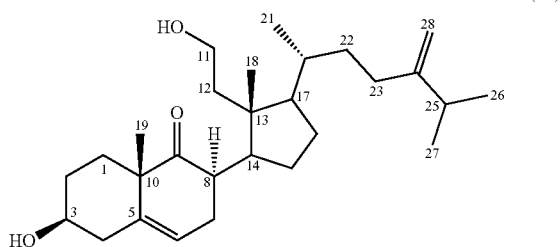

or 8β-H-3β,11-dihydroxy-24-methylene-9,11-secocholest-5-en-9-one with a chemical formula (V):

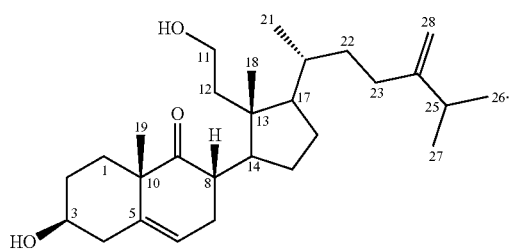

In a preferred embodiment, the 9,11-secosteroids in the present invention is extracted from soft corals.

In a more preferred embodiment, the 9,11-secosteroids in the present invention is extracted from soft coral *Sinularia leptoclados*.

In a preferred embodiment, the effective amount of 9,11-secosteroids is 1~10 μM.

In a more preferred embodiment, the effective amount of 9,11-secosteroids is 1.63~8.07 μM.

DESCRIPTION OF EMBODIMENTS

The examples below are non-limiting and are merely representative of various aspects and features of the present invention.

1. Materials and Experiments 1.1 Selection of Marine Biomaterials

The marine biomaterials used herein is soft coral, more preferred, the soft coral is *Sinularia leptoclados*.

In November 2018, samples of the soft coral *Sinularia leptoclados* were obtained by hand using self-contained underwater breathing apparatus (SCUBA) off the coast of Pingtung, Taiwan. The samples were stored in a freezer at −20° C. until extraction. A specimen voucher was deposited with the Research Center for Chinese Herbal Medicine, Chang Gung University of Science and Technology, Taiwan (specimen No.: CGUST-0004-2018-NOV).

1.2 Sample Extraction and Isolation

In the embodiment of the invention, soft coral material (wet weight 1742 g, dry weight 488 g) was cut into small pieces prior to ethyl acetate (EtOAc) extraction at room temperature, then an EtOAc layer mixture was obtained. The EtOAc layer mixture (9.6 g; superoxide anion generation: $IC_{50}$ 3.97 μg/mL; elastase release: $IC_{50}$>10 μg/mL) was separated on silica gel column and eluted using n-hexane/EtOAc (stepwise, pure n-hexane-pure EtOAc-pure MeOH) to yield 22 fractions A-V.

Among these fractions, the fraction P (superoxide anion generation: $IC_{50}$ 3.57 μg/mL; elastase release: $IC_{50}$ 6.80 μg/mL) was further separated by reversed-phase medium pressure liquid chromatography (RP-MPLC) using a mixture of MeOH/ddH$_2$O ($V_{MeOH}$:$V_{ddH2O}$=90:10 of volume ratio at a flow rate of 8.0 mL/min) to obtain compound 7 (82.5 mg) and nine subfractions, P1-P9.

The subfraction P3 (superoxide anion generation: $IC_{50}$ 2.06 μg/mL; elastase release: $IC_{50}$ 1.45 μg/mL) was repurified by reversed-phase high-performance liquid chromatography (RP-HPLC) using a mixture of acetonitrile/ddH$_2$O ($V_{Acetonitrile}$:$V_{ddH2O}$=90:10 at a flow rate of 2.0 mL/min) to obtain compound 1 (2.6 mg), compound 2 (2.0 mg), compound 3 (3.5 mg), compound 4 (100.4 mg) and compound 5 (13.3 mg).

Subfraction P4 was purified by RP-HPLC using a mixture of MeOH/ddH$_2$O ($V_{MeOH}$: $V_{ddH2O}$=90:10 at a flow rate of 2.0 mL/min) to yield compound 6 (6.8 mg).

1.3 In Vitro Anti-Inflammatory Bioassay 1.3.1 Human Neutrophil Superoxide Anion Generation and Elastase Release Blood samples were collected from healthy adult donors (20-32 years) via venipuncture in accordance with the standard protocol approved by the local institutional review board. Human neutrophils were isolated from peripheral blood through dextran sedimentation, centrifugation in a Ficoll-Hypaque gradient, and hypotonic lysis of red blood cells.

In accordance with the above-mentioned protocol, assays were performed to measure superoxide anion generation based on the superoxide dismutase-inhibitable reduction of ferricytochrome c; methoxy-succinyl-alanyl-alanyl-prolyl-valine-p-nitroanilide (MeO-Suc-Ala-Ala-Pro-Val-p-nitroanilide) was used as the enzyme substrate for the detection of elastase release.

1.3.2 Receptor Binding Assay

Receptor binding assays of the present invention were performed via FACScan™ flow Cytometer analysis of N-formyl-Nle-Leu-Phe-Nle-Tyr-Lys-fluorescein (fNLFNYK; a fluorescent analog of N-formylmethionyl-leucyl-phenylalanine (fMLF)) binding to receptor of human neutrophils; The neutrophils were preincubated with test compounds at 4° C. for 5 min and then labelled with fNLFNYK for 30 min, then the cells were immediately analyzed via flow cytometry.

1.4 Statistical Analysis

All experiments were conducted at least three times and the results are presented as the mean±SEM. Statistical analysis was performed using the Student's t-test, and a p value<0.05 was considered as statistically significant. Sigmaplot software (version 8.0, Systat Software, San Jose, CA, USA) was used for all statistical analysis.

2. Results

2.1 $^1$H NMR-Based Isolation of Anti-Inflammatory 9,11-Secosteroids

In the present invention, primary silica gel chromatographic fractionation was used to probe anti-inflammatory 9,11-secosteroids within the organic extract from *Sinularia leptoclados*. Comprehensive chemical and biological profiles of all fractions (fractions A-V) were then constructed through $^1$H-NMR analysis and an examination of anti-inflammatory activity (see FIG. 1).

Fraction P was selected for subsequent analysis due to its characteristic 9,11-secosteroidal $^1$H-NMR patterns (δH 3.51, 1H, in, H-3; 3.03, 1H, ddd, J=12.4, 12.8, 6.8, H-8; 3.86, 1H, in; 3.74, 1H, in, H$_2$-11) and potent anti-inflammatory activities (superoxide anion generation: IC$_{50}$ 3.57 μg/mL; elastase release: IC$_{50}$ 6.80 μg/mL).

Figure 2:
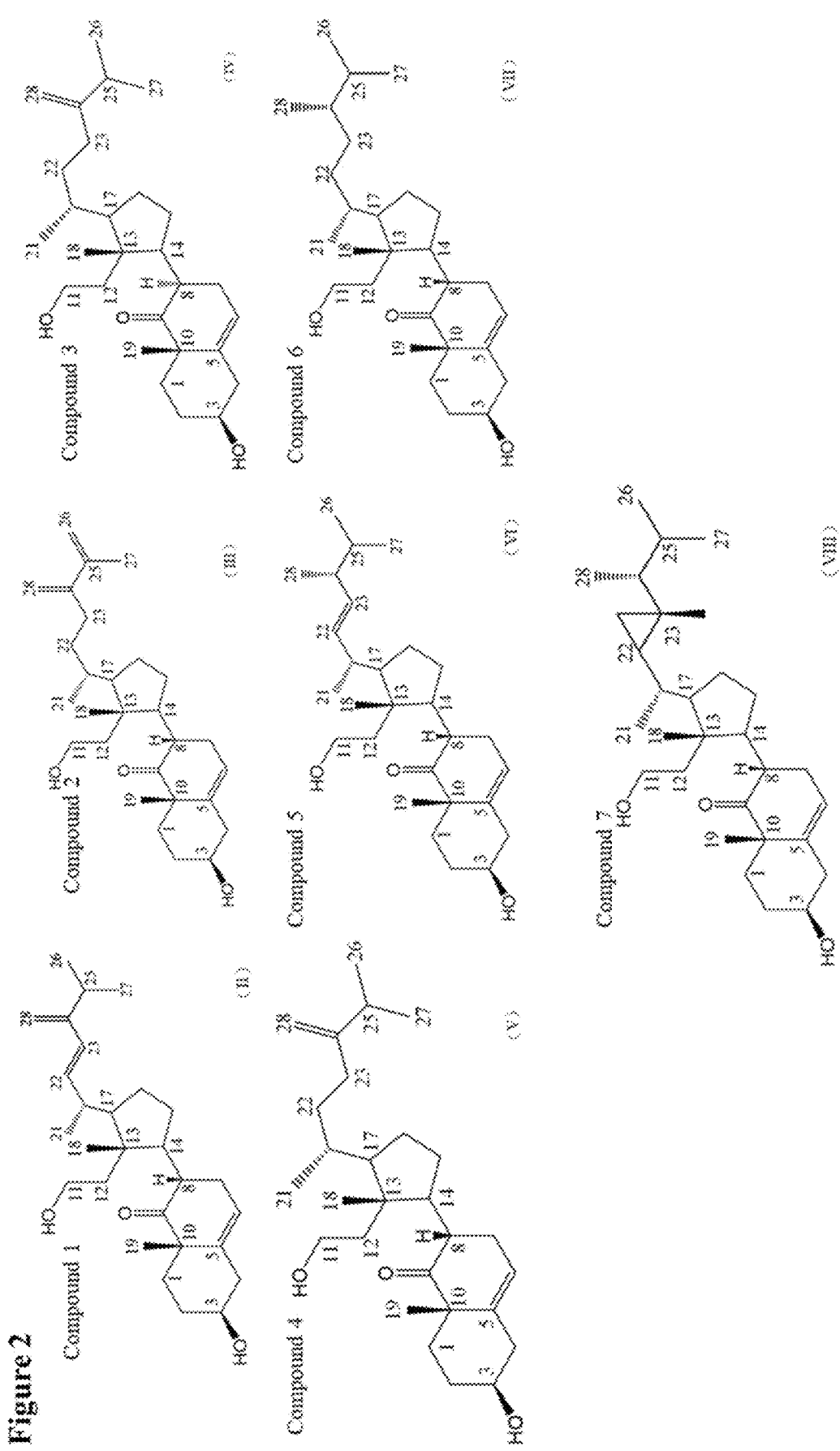
FIG. 2 illustrates the chemical structures of the seven 9,11-secosteroids isolated by the invention.

Consecutive column chromatographic processes (RP-HPLC and RP-HPLC) resulted in the isolation of two novel 9,11-secosteroids, compound 1 with chemical formula (II) and compound 2 with chemical formula (III), as well as five known 9,11-secosteroids, compounds 3-7 with chemical formulae (IV)-(VIII), see FIG. 2.

2.2 Chemical Identification of 9,11-Secosterols

Figure 3:
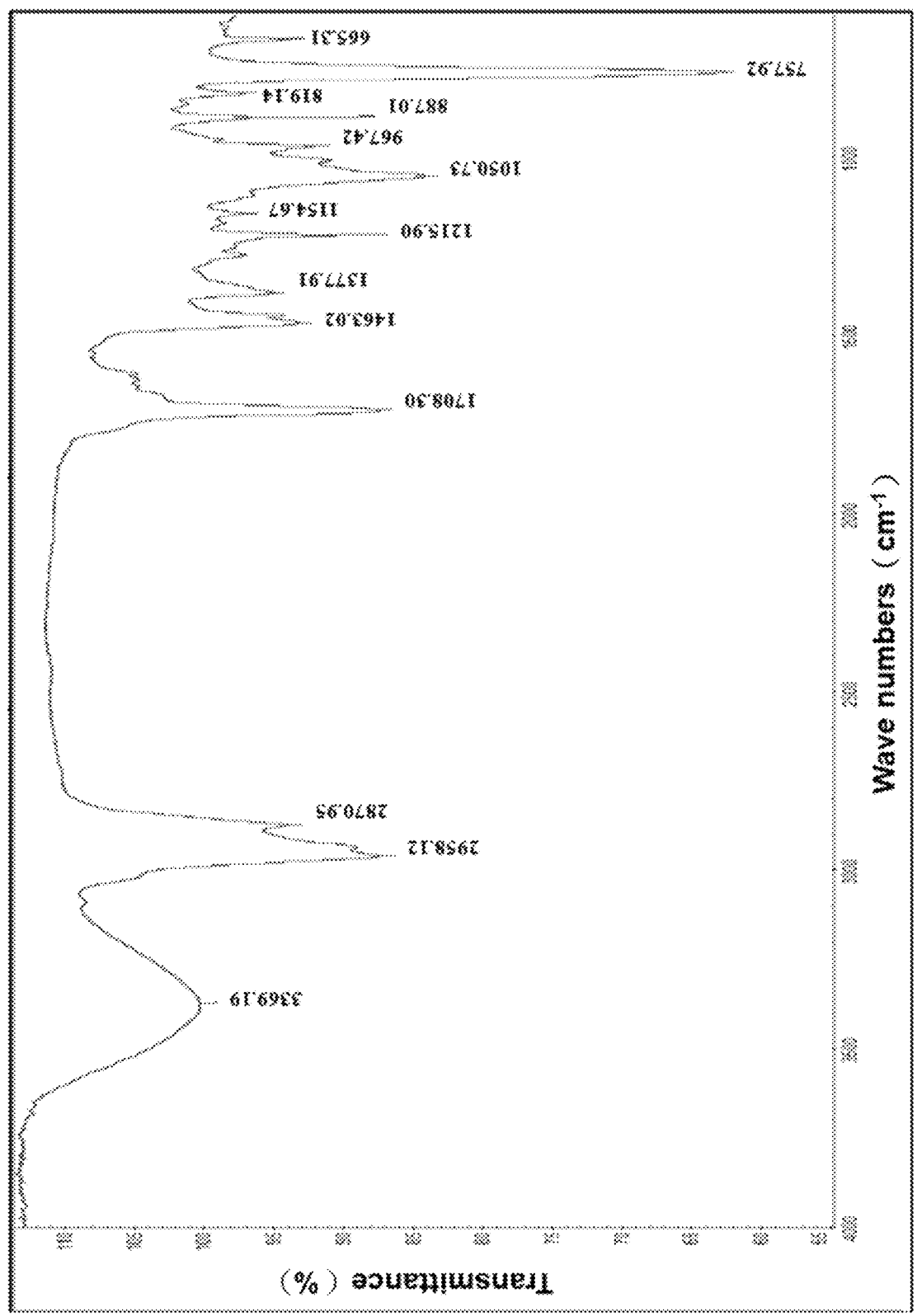
FIG. 3 illustrates the infrared spectrum of compound 1.

By the foregoing method in the present invention, compound 1 was obtained as a colorless oil. Positive mode high resolution electrospray ionization mass spectrum ((+)-HRESIMS) of compound 1 revealed a sodiated adduct ion peak at m/z 451.31811, which established the molecular formula $C_{28}H_{44}O_3$ (calcd. for $C_{28}H_{44}O_3$+Na, 451.31827), indicating seven degrees of unsaturation; IR absorption of compound 1 was observed at 3369, 2958, and 1708 cm$^{-1}$ suggested the presence of hydroxy, alkene, and ketonic groups in compound 1 (see FIG. 3).

The $^{13}$C and distortionless enhancement by polarization transfer (DEPT) spectroscopic data revealed 28 carbon signals in compound 1, including five methyls, eight sp$^3$ methylenes (including an oxymethylene), one sp$^2$ methylene, six sp$^3$ methines (including one oxymethine), two sp$^3$ quaternary carbons, three sp$^2$ methines, and three sp$^2$ quaternary carbons (including two olefin carbons and one ketonic carbonyl). It was found that the quaternary carbon signal at δ$_C$ 217.5 (C-9) and the proton shifts at δ$_H$ 1.40 (s, H$_3$-19), 3.03 (ddd, J=12.4, 12.4, 6.8 Hz, H-8), 3.51 (in, H-3), and 5.47 (d, J=5.6 Hz, H-6) of compound 1 were similar to those of 3-hydroxy-9,11-seco-9-oxosterols (with a 5,6-double bond), a disubstituted alkene was recognized within the carbon signals at δ$_C$ 134.6 (CH-22) and 130.2 (CH-23), and was further confirmed by two olefin proton signals at δ$_H$ 5.65 (1H, dd, J=16.0, 7.2 Hz, H-22) and 5.93 (1H, d, J=16.0 Hz, H-23) (see Table 1). Three methyl doublets at δ$_H$ 1.08 (3H, J=6.4 Hz), 1.06 (3H, J=6.8 Hz), and 1.07 (3H, J=6.8 Hz) can respectively be attributed to the Me-21, Me-26, and Me-27 methyl groups. Two sharp methyl singlets for H$_3$-18 and H$_3$-19 respectively appeared at δ$_H$ 0.69 (3H, s) and 1.40 (3H, s). Given the above, these findings identify compound 1 as a tricyclic compound.

The correlation spectroscopy (COSY) data and the key heteronuclear multiple bond correlation (HMBC) between protons and quaternary carbons of the compound 1, such as H-4, H$_2$-7, H$_3$-19/C-5; H-8, H-14, H$_3$-19/C-9; H-6, H$_3$-19/C-10; H$_2$-12, H$_3$-18/C-13 and H-22, H-23, H-25, H$_3$-26, H$_3$-27, H$_2$-28/C-24, permitted elucidation of the carbon skeleton of compound 1 (see Table 1).

TABLE 1

$^1$H (400 MHz, CDCl$_3$) and $^{13}$C (100 MHz, CDCl$_3$) NMR data and COSY and HMBC for compound 1.

| Position | δ$_H$ (J in Hz) | δ$_C$, Type | COSY | HMBC |
|---|---|---|---|---|
| 1a/b | 1.50 m; 1.81 m | 31.0, CH$_2$ | H$_2$-2 | C-3 |
| 2a/b | 1.40 m; 1.93 m | 30.8, CH$_2$ | H$_2$-1, H-3 | n.o.$^a$ |
| 3 | 3.51 m | 71.4, CH | H$_2$-2, H$_2$-4 | n.o. |
| 4a/b | 2.23 m; 2.44 m | 40.6, CH$_2$ | H-3 | C-3, C-5, C-6 |
| 5 | — | 140.4, C | — | — |
| 6 | 5.47 brd (5.6) | 121.5, CH | H$_2$-7 | C-4, C-7, C-8, C-10 |
| 7a/b | 1.98 m; 2.40 m | 33.1, CH$_2$ | H-6, H-8 | C-5, C-6 |
| 8 | 3.03 ddd (12.4, 12.4, 6.8) | 43.8, CH | H$_2$-7, H-14 | C-7, C-9, C-14 |
| 9 | — | 217.5, C | — | — |
| 10 | — | 48.4, C | — | — |
| 11a/b | 3.86 m; 3.74 m | 59.4, CH$_2$ | H$_2$-12 | n.o. |
| 12 | 1.33 m; 1.67 m | 40.2, CH$_2$ | H$_2$-11 | C-11, C-13 |
| 13 | — | 45.5, C | — | — |
| 14 | 2.61 m | 42.1, CH | H-8, H$_2$-15 | C-9 |
| 15 | 1.31 m; 1.58 m | 24.6, CH$_2$ | H-14, H$_2$-16 | C-14 |
| 16 | 1.31 m; 1.71 m | 24.8, CH$_2$ | H$_2$-15, H-17 | n.o. |
| 17 | 1.78 m | 49.6, CH | H$_2$-16, H-20 | n.o. |
| 18 | 0.69 s | 17.7, CH$_3$ | — | C-12, C-13, C-14, C-17 |
| 19 | 1.40 s | 22.8, CH$_3$ | — | C-1, C-5, C-9, C-10 |
| 20 | 2.25 m | 38.5, CH | H-17, H$_3$-21, H-22 | C-16 |
| 21 | 1.08 d (6.4) | 22.1, CH$_3$ | H-20 | C-17, C-20 |
| 22 | 5.65 dd (16.0, 7.2) | 134.6, CH | H-20, H-23 | C-20, C-21, C-24 |
| 23 | 5.93 d (16.0) | 130.2, CH | H-22 | C-20, C-24, C-25, C-28 |
| 24 | — | 153.0, C | — | — |
| 25 | 2.54 m | 29.4, CH | H$_3$-26, H$_3$-27 | C-24, C-28 |
| 26 | 1.06 d (6.8) | 22.4, CH$_3$ | H-25 | C-24, C-25 |
| 27 | 1.07 d (6.8) | 21.5, CH$_3$ | H-25 | C-24, C-25 |
| 28 | 4.83 d (6.8) | 109.8, CH$_2$ | | C-24, C-25 | n.o. = not observed.

Figure 4:
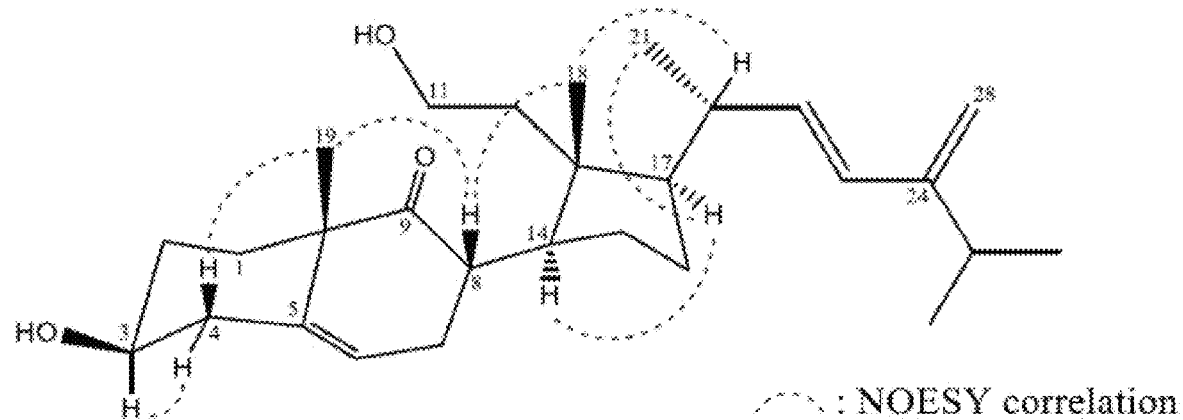
FIG. 4 illustrates the correlations observed for compound 1 under nuclear Overhauser effect spectroscopy (NOESY) analysis.

The relative stereochemistry of compound 1 was explained in terms of correlations observed in a nuclear Overhauser effect spectroscopy (NOESY) experiment, and through a comparison of NMR data between the compound 1 and known secosterol 5. The results suggest that these two compounds possess the same 9,11-secosterol skeleton as well as the same core A-, B-, and D-rings, and the configurations at C-3, C-8, C-10, C-13, C-14, and C-17 in compound 1 were found to be identical to those of secosterol 5; furthermore, key NOESY correlations for compound 1 displayed interactions between H-8/H$_3$-18 and H-8/H$_3$-19. Thus, H-8 should be located on the β-face and a large coupling constant (J=16.0 Hz) indicated a trans relationship between H-22 and H-23. (see FIG. 4).

The molecular formula of compound 2 was the same as that of compound 1 ($C_{28}H_{44}O_3$), with seven degrees of unsaturation. Its IR bands revealed the presence of hydroxy (3406 cm$^{-1}$) and ketone (1708 cm$^{-1}$) groups. After the comparison of one-dimensional and two-dimensional NMR experiments on compound 2 (see Table 2), the core structural systems of compound 2 were established. It was found that the $^1$H and $^{13}$C NMR chemical shifts of compound 2 (including coupling patterns and coupling constants) resembled those of compound 1; however, the signals corresponding to the disubstituted alkene between C-22/23 in compound 1 were replaced by aliphatic methylenes in compound 2, and one of the methyl groups at C-25 in compound 1 (Me-26) was replaced by an exocyclic carbon-carbon bond in compound 2.

1, which were in agreement with the observed $^1$H and $^{13}$C NMR chemical shifts and proton coupling constants.

Given the above, as shown in FIG. 2, the compound 1 was unambiguously identified and it was named sinleptosterol A, which was a colorless oil, and its physical and chemical properties were: $[\alpha]_D^{22}$ −16.31 (c 0.095, CHCl$_3$); IR (neat) $\nu_{max}$ 3369, 2958, 1708 cm$^{-1}$; $^1$H (400 MHz, CDCl$_3$) and $^{13}$C (100 MHz, CDCl$_3$) NMR data (see Table 1); ESIMS: m/z 451 [M+Na]$^+$; HRESIMS: m/z 451.31811 (calcd. for $C_{28}H_{44}O_3$+Na, 451.31827).

The compound 2 was unambiguously identified and it was named sinleptosterol B, which was a colorless oil, and its physical and chemical properties were: $[\alpha]_D^{24}$ −36 (c 0.1, CHCl$_3$); IR (neat) $\nu_{max}$ 3406, 2954, 1708 cm$^{-1}$; $^1$H (400 MHz, CDCl$_3$) and $^{13}$C (100 MHz, CDCl$_3$) NMR data (see Table 2); ESIMS: m/z 451 [M+Na]$^+$; HRESIMS: m/z 451.3239 (calcd. for $C_{28}H_{44}O_3$+Na, 451.3188).

The five known 9,11-secosteroids compounds (compounds 3-7) were, respectively: 8αH-3β,11-dihydroxy-24-methylene-9,11-secocholest-5-en-9-one (compound 3), 8βH-3β,11-dihydroxy-24-methylene-9,11-secocholest-5-en-9-one (compound 4), leptosterol A (compound 5), (24S)-3β,11-dihydroxy-24-methyl-9,11-secocholest-5-en-9-one (compound 6), and 3β,11-dihydroxy-9,11-secogorgost-5-en-9-one (compound 7).

TABLE 2

$^1$H (400 MHz, CDCl$_3$) and $^{13}$C (100 MHz, CDCl$_3$) NMR data and COSY and HMBC for compound 2.

| Position | $\delta_H$ (J in Hz) | $\delta_C$, Type | COSY | HMBC |
|---|---|---|---|---|
| 1a/b | 1.53 m; 1.90 m | 30.8, CH$_2$ | H$_2$-2 | n.o. |
| 2a/b | 1.31 m; 1.93 m | 31.3, CH$_2$ | H$_2$-1, H-3 | n.o. |
| 3 | 3.51 m | 71.4, CH | H$_2$-2, H$_2$-4 | n.o. |
| 4a/b | 2.23 m; 2.44 m | 40.6, CH$_2$ | H-3 | n.o. |
| 5 | — | 140.4, C | — | — |
| 6 | 5.48 brd (5.6) | 121.5, CH | H$_2$-7 | C-4, C-7, C-8 |
| 7a/b | 2.02 m; 2.39 m | 33.0, CH$_2$ | H-6, H-8 | n.o. |
| 8 | 3.03 td (12.4, 6.8) | 43.6, CH | H$_2$-7, H-14 | C-7, C-9, C-14 |
| 9 | — | 217.5, C | — | — |
| 10 | — | 48.5, C | — | — |
| 11a/b | 3.69 m; 3.83 m | 59.4, CH$_2$ | H$_2$-12 | n.o. |
| 12 | 1.32 m; 1.68 m | 40.3, CH$_2$ | H$_2$-11 | n.o. |
| 13 | — | 45.6, C | — | — |
| 14 | 2.61 m | 41.8, CH | H-8, H$_2$-15 | n.o. |
| 15 | 1.30 m; 1.56 m | 24.4, CH$_2$ | H-14, H$_2$-16 | n.o. |
| 16 | 1.30 m; 1.74 m | 25.0, CH$_2$ | H$_2$-15, H-17 | — |
| 17 | 1.65 m | 49.2, CH | H$_2$-16 | — |
| 18 | 0.67 s | 17.3, CH$_3$ | — | C-11, C-12, C-13, C-14, C-17 |
| 19 | 1.38 s | 22.9, CH$_3$ | — | C-1, C-5, C-9, C-10 |
| 20 | 1.41 m | 34.0, CH | H$_3$-21 | n.o. |
| 21 | 1.01 d (6.8) | 19.4, CH$_3$ | H-20 | C-17, C-20, C-22 |
| 22 | 1.17m; 1.51 m | 34.7, CH$_2$ | H-23 | n.o. |
| 23 | 1.81 m; 2.39 m | 31.0, CH$_2$ | H-22 | n.o. |
| 24 | — | 148.5, C | — | |
| 25 | — | 142.7, C | — | |
| 26 | 4.59 d (1.2) | 112.5, CH$_2$ | — | C-25 |
| 27 | 1.90 s | 21.2, CH$_3$ | — | C-24, C-25, C-26 |
| 28 | 5.06 s | 112.0, CH$_2$ | — | C-23, C-24, C-25 | n.o. = not observed.

Moreover, in the present invention, the observed HMBC correlations of compound 2 fully supported the locations of the functional groups. An olefinic bond was located at C-25/26 from H$_2$-26, H$_3$-27, H$_3$-28 to C-25, respectively, and the relative configurations at C-3, C-8, C-10, C-13, C-14, and C-17 of compound 2 were found to be the same as those of 1 in the core rings A-C. Note that the stereogenic carbons of compound 2 were identical to those of compound 2.3 Anti-Inflammatory Assessment of Isolated 9,11-Secosterols In the present invention, the anti-inflammatory properties of compounds 1-7 were characterized by assessing the inhibition of superoxide anion generation and elastase release by human neutrophils in response to fMLP/CB.

The results demonstrated that the IC$_{50}$ values of compounds 1-5 were shown to inhibit superoxide anion genera tion and elastase release, at concentrations ranging from 1.63 to 8.07 μM. The $IC_{50}$ values of compounds 3 and 4 were lower than the other isolates. compound 7 presented activity at a concentration of 10 μM, indicating that the unique gorgosterol side chain nullified the anti-inflammatory activities (see Table 3).

TABLE 3

Effects of compounds 1-7 on superoxide anion generation and elastase release in fMLF/CB-induced human neutrophils.

| Compound | Superoxide Anion | | Elastase Release | |
|---|---|---|---|---|
| | $IC_{50}$ (μM) | Inhibition (%) | $IC_{50}$ (μM) | Inhibition (%) |
| 1 | 7.07 ± 0.52 | 64.76 ± 3.42 *** | 7.57 ± 0.40 | 65.04 ± 2.76 *** |
| 2 | 4.68 ± 0.57 | 76.30 ± 5.09 *** | 4.29 ± 0.25 | 105.09 ± 5.25 *** |
| 3 | 1.97 ± 0.12 | 90.47 ± 2.44 *** | 3.12 ± 0.07 | 112.23 ± 5.01 *** |
| 4 | 2.96 ± 0.91 | 91.11 ± 4.51 *** | 1.63 ± 0.15 | 93.74 ± 1.23 *** |
| 5 | 8.07 ± 0.53 | 57.93 ± 2.30 *** | 4.73 ± 0.57 | 86.32 ± 2.91 *** |
| 6 | 4.09 ± 0.50 | 60.51 ± 4.06 *** | >10 | 25.38 ± 6.68 ** |
| 7 | >10 | 10.29 ± 5.42 *** | >10 | 18.87 ± 3.86 *** |

Percentage of inhibition at 10 μM concentration.
Results are presented as mean ± S.E.M. (n = 3 or 4).
** p < 0.01,
*** p < 0.001 compared with the control (DMSO).
Concentration necessary for 50% inhibition ($IC_{50}$)

N-Formyl peptide receptors (FPRs) are a family of G-protein coupled receptors involved in the switching on of leucocyte responses during inflammation. Human FPR1 is expressed primarily in neutrophils, monocytes, and macrophages. It also initiates immune reactions in response to several formyl peptide ligands derived from bacteria or mitochondria.

Researchers have previously proven that compounds acting as FPR1 antagonists exhibit anti-inflammatory activity in vitro and in vivo, therefore, flow cytometry was used to determine whether compounds 1-7 possess binding affinity to FPR1 in the present invention.

Figure 5:
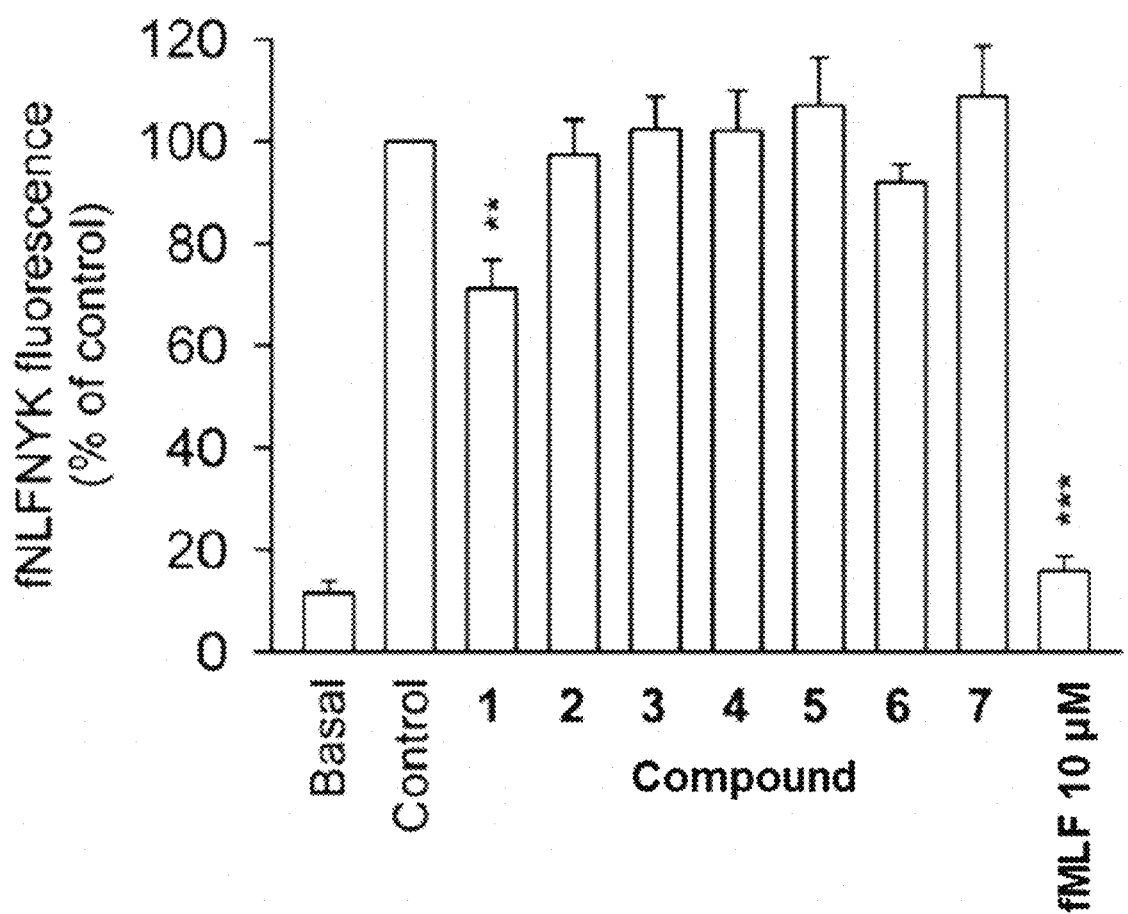
FIG. 5 illustrates the FPR1 receptor binding assay of compounds 1~7 in human neutrophils.

The receptor-binding assay is based on the binding between N-formyl-Nle-Leu-Phe-Nle-Tyr-Lys-fluorescein (fNLFNYK) and the FRP1 receptor of human neutrophil. The results revealed that fMLF (10 μM) entirely inhibited the binding of fNLFNYK (2 nM), whereas only compound 1 presented a low affinity toward the FPR1 receptor at a concentration of 10 μM (see FIG. 5).

What is claimed is:

1. A method for inhibiting inflammation, comprising: administering a pharmaceutical in a subject suffering from inflammation, wherein the pharmaceutical composition comprises an effective amount of 9,11-secosteroids; wherein the 9,11-secosteroids having a chemical formula (I)

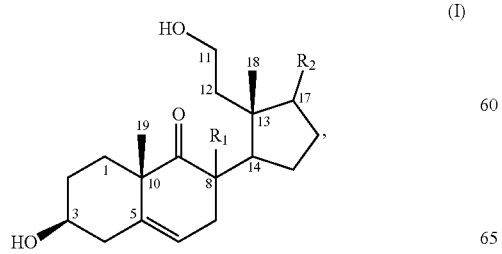

(I)

while R1 is α-H, R2 is

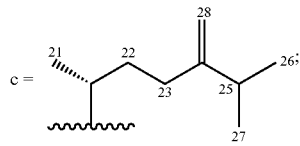

and while R1 is β-H, R2 is selected from

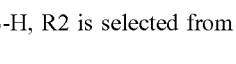

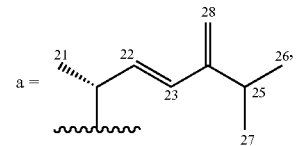

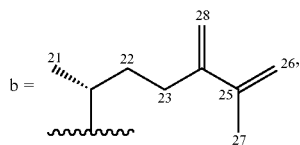

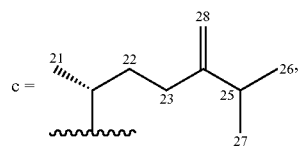

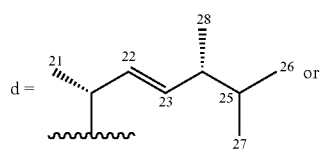

-continued e = 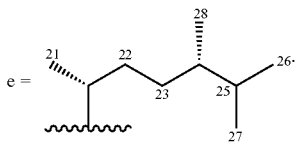

wherein the inflammation is caused by a bacterial peptide comprising N-formylmethionyl-leucyl-phenylalanine (fMLF).

2. The method of claim 1, wherein the 9,11-secosteroids is 8α-H-3β,11-dihydroxy-24-methylene-9,11-secocholest-5-en-9-one with a chemical formula (IV):

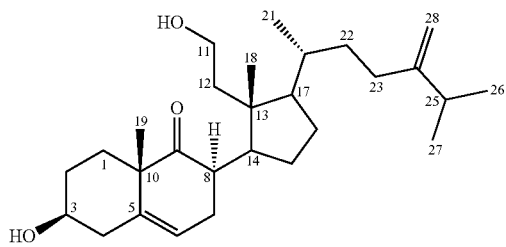

or 8β-H-3β,11-dihydroxy-24-methylene-9,11-secocholest-5-en-9-one with a chemical formula (V):

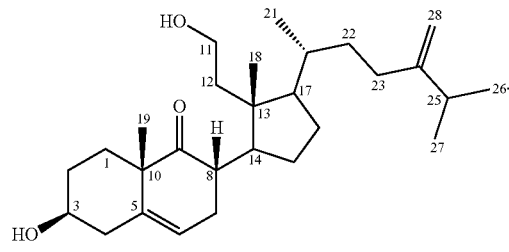

3. The method of claim 1, wherein the 9,11-secosteroids inhibits inflammation via inhibiting the superoxide anion generation by human neutrophils.

4. The method of claim 1, wherein the 9,11-secosteroids inhibits inflammation via inhibiting the elastase release by human neutrophils.

5. The method of claim 1, wherein the effective amount of 9,11-secosteroids is 1~10 μM.

6. The method of claim 1, wherein the effective amount of 9,11-secosteroids is 1.63~8.07 μM.

* * * * *